United States Patent [19]
Antkowiak et al.

[11] Patent Number: 5,610,227
[45] Date of Patent: Mar. 11, 1997

[54] LITHIUM AMINO MAGNESIATE POLYMERIZATION INITIATORS AND ELASTOMERS HAVING REDUCED HYSTERESIS

[75] Inventors: Thomas A. Antkowiak, Wadsworth; James E. Hall, Mogadore, both of Ohio

[73] Assignee: Bridgestone/Firestone, Inc., Tokyo, Japan

[21] Appl. No.: 487,349

[22] Filed: Jun. 7, 1995

[51] Int. Cl.$^6$ .............................. C08K 3/04; C08F 4/50; C08F 36/04
[52] U.S. Cl. ................ 524/572; 524/573; 524/575; 525/332.3; 525/332.9; 525/371; 525/375; 525/379; 525/384; 526/180; 526/183; 526/204; 526/340; 502/155; 502/167; 260/665 R; 540/450; 540/596; 540/612; 546/184; 546/186; 546/191; 546/208; 546/210; 546/192; 546/11; 546/4; 548/400; 548/579; 564/487; 152/450
[58] Field of Search .................. 260/665 R; 540/450, 540/596, 597, 612; 546/184, 186, 208, 275, 281, 348; 548/523, 579, 400; 564/413, 487; 502/153, 155, 157, 167; 526/173, 180, 217, 340, 183, 204; 524/572, 573, 575; 525/332.3, 332.9, 371, 375, 379, 384

[56] References Cited

U.S. PATENT DOCUMENTS

| | | |
|---|---|---|
| 4,070,344 | 1/1978 | Hergenrother . |
| 4,139,490 | 2/1979 | Halasa . |
| 4,174,431 | 11/1979 | Halasa . |
| 4,401,800 | 8/1983 | Hall . |
| 4,410,742 | 10/1983 | Mueller ............................ 526/183 X |
| 4,429,091 | 1/1984 | Hall . |
| 4,476,240 | 10/1984 | Hall . |
| 4,480,075 | 10/1984 | Willis . |
| 4,520,123 | 5/1985 | Hall . |
| 4,530,984 | 7/1985 | Hall . |
| 4,634,786 | 1/1987 | Kamienski . |
| 4,672,097 | 6/1987 | Hall . |
| 4,748,283 | 5/1988 | Kamienski . |
| 4,861,742 | 8/1989 | Bronstert . |
| 4,960,842 | 10/1990 | Lo . |
| 5,066,729 | 11/1991 | Stayer . |
| 5,238,893 | 8/1993 | Hergenrother . |
| 5,268,413 | 12/1993 | Antkowiak . |
| 5,268,439 | 12/1993 | Hergenrother . |
| 5,320,774 | 6/1994 | Mehta . |
| 5,321,093 | 6/1994 | Bronstert . |
| 5,329,005 | 7/1994 | Lawson . |
| 5,332,810 | 7/1994 | Lawson . |
| 5,354,822 | 10/1994 | Antkowiak . |
| 5,393,721 | 2/1995 | Kitamura . |

FOREIGN PATENT DOCUMENTS

| | | | |
|---|---|---|---|
| 0316255A2 | 5/1989 | European Pat. Off. . | |
| 4537789 | 11/1970 | Japan | ........................... 526/183 |
| 4603388 | 1/1971 | Japan | ........................... 526/180 |
| 4618485 | 5/1971 | Japan | ........................... 526/183 |

OTHER PUBLICATIONS

Hsieh, H. L. and Wang, I. W., Effects of Dibutylmagnesium on Alkyllithium–Initiated Polymerizations. Macromolecules 19, pp. 299–403, 1986.

Elastomers, Synthetic (SBR) in Kirk–Othmer Encyclopedia of Chemical Technology, vol. 8, Third Ed., pp. 608–625. John Wiley & Sons, New York. 1979.

English translation of Japanese Kokoku 46–3388.

*Primary Examiner*—Fred Teskin
*Attorney, Agent, or Firm*—Daniel N. Hall

[57] ABSTRACT

The present invention provides anionic polymerization initiators, comprising lithium amino magnesiate complexes, resulting in diene polymer and copolymer elastomers. The invention initiators have stable living ends at high polymerization temperatures and produce polymers containing a high level of tertiary amine functionality. Such polymers exhibit an increased efficiency in coupling termination reactions, and elastomers and products prepared from such polymers exhibit reduced hysteresis properties. Methods are also provided for preparing the initiators, the polymers and the elastomers.

23 Claims, No Drawings

LITHIUM AMINO MAGNESIATE POLYMERIZATION INITIATORS AND ELASTOMERS HAVING REDUCED HYSTERESIS

BACKGROUND OF INVENTION

The subject invention relates to anionic polymerization resulting in diene polymer and copolymer elastomers. More particularly, the invention relates to lithium amino magnesiate initiators which are stable at high polymerization temperatures and produce polymers containing a high level of tertiary amine functionality, and elastomers exhibiting reduced hysteresis properties.

When conducting polymerization on a commercial basis, it is desirable to increase the efficiency of polymerization reactions by increasing the number of monomers which can be incorporated into the polymer chain in a given time period. This may be accomplished by utilizing high temperatures during polymerization. When employing anionic polymerization initiators, such a system requires that the initiators be stable at high temperatures and capable of producing chain-end functionalized polymers, having a narrow molecular weight distribution, which can be compounded to produce elastomers exhibiting reduced hysteresis properties. Such elastomers, when compounded to form articles, such as tires, power belts and the like, will show an increase in rebound, a decrease in rolling resistance and have less heat build-up when mechanical stresses are applied.

Previous attempts at preparing reduced hysteresis compounds have included high temperature mixing of the filler-rubber mixtures in the presence of selectively-reactive promoters to promote compounding material reinforcement, surface oxidation of the compounding materials, and chemical modifications to the terminal end of polymers using tetramethyldiamino-benzophenone (Michler's ketone), tin coupling agents and the like, and surface grafting thereon. All of these approaches have focused upon increased interaction between the elastomer and the compounding materials.

It has also been recognized that carbon black, employed as a reinforcing filler in rubber compounds, should be well dispersed throughout the rubber in order to improve various physical properties. This dispersion can be achieved, for instance, by end capping polydienes by reacting a metal terminated polydiene with a capping agent, such as a halogenated nitrile, a heterocyclic aromatic nitrogen-containing compound or an alkyl benzoate. Additionally, it is known in the art that both ends of the polydiene chains can be capped with polar groups by utilizing functionalized anionic initiators, such as lithium amides.

The present invention provides novel initiators for anionic polymerization, to form elastomers with functional groups derived from said initiators. The functional groups are incorporated at the polymer chain ends, providing improved dispersability of carbon black throughout the elastomeric composition during compounding. As will be described herein below, the functional groups are cyclic amine substituents of the initiators which comprise lithium amino magnesiate complexes. In the polymer, the cyclic amine substituent is incorporated at one end of the polymer chain and the magnesium atom is complexed to the lithium atom and the magnesium-lithium complex is carried at the other ("living") end of the polymer chain prior to quenching.

Lithium amino initiators containing functionalizing agents, such as substituted aldimines, ketimines and secondary amines, are known in the art to produce low hysteresis rubbers. It is also known in the art that magnesium dihydrocarbyl compounds, while not by themselves effective polymerization initiators for diene and styrene polymerization, can participate in polymerization when complexed either with an alkyl lithium initiator or with the propagating polymer-lithium molecules. Magnesium dihydrocarbyl compounds have been utilized, in combination with alkali metal compounds, such as lithium, sodium and potassium alkyl sulfides, amines, amides and acetylides, to produce anionic type initiators.

However, when lithium amide initiators are used at high polymerization temperatures it is difficult to maintain the "living" ends or the polymer-lithium bonds needed for efficient polymerization and termination reactions. With known initiators it has been found that the lithium constituent will often be involved in metalation reactions or combine with an available alpha-hydrogen atom, resulting in lithium hydride, especially at elevated temperatures, thereby destroying the initiator and causing additional harmful side reactions. Hence, high temperature polymerizations have proven to be difficult to maintain and difficult to terminate efficiently.

A need exists, therefore, for an improved polymerization initiator which, when employed in an anionic polymerization, will result in polymers with chain ends having functional groups derived from the initiator. Further, a need exists for such an initiator that will perform effectively at high polymerization temperatures resulting in narrow molecular weight distribution polymers and the retention of "living" ends.

SUMMARY OF INVENTION

The present invention provides anionic polymerization initiators which are stable at high polymerization temperatures and which promote the incorporation of functional tertiary amine groups, derived from the initiators, in the polymer chain. The invention also provides a method for preparing these initiators. In addition, the invention provides a functionalized polymer derived from the initiators, a method of preparing such a functionalized polymer, and a method for polymerization of the polymer at high temperatures. The advantages of the present invention over the prior art will become apparent from the specification and claims which follow.

In general, an anionic polymerization initiator of the present invention comprises a lithium amino magnesiate complex having the general formula

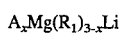

where A is selected from the group consisting of cyclic amine substituents having the general formula

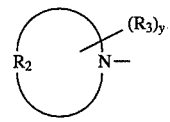

where x is the integer 2 or 3; the A substituents are the same or mixtures of different substituents; $R_2$ is from about 3 to about 20 methylene groups; $R_1$ and $R_3$, which can be the same or different from one another, are selected from the group consisting of alkyls, cycloalkyls, alkenyls, alkynyls, aryls and aralkyls, having from 1 to about 20 carbon atoms; y is an integer of from zero to about 10; and where y is greater than zero, the $R_3$ substituents are the same or mixtures of different substituents.

There is also provided a method of preparing an anionic polymerization initiator, which comprises reacting an organolithium compound having the general formula $R_1Li$, with a magnesium dicyclic amide having the general formula $A_2Mg$, to form a reaction product having the general formula

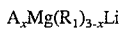

where A is selected from the group consisting of cyclic amine substituents having the general formula

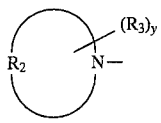

where x is the integer 2 or 3; and wherein when x is 2, the organolithium compound is selected from the group consisting of lithium alkyls, cycloalkyls, alkenyls, alkynyls, aryls and aralkyls having from 1 to about 20 carbon atoms, and the method further comprises the step of reacting the reaction product with compound AH, wherein AH is the cyclic amine form of A; and wherein when x is 3, the organolithium compound is A-lithium; $R_2$, $R_3$ and y are as described herein above; and the A substituents are the same or mixtures of different substituents.

A polymer according to the invention comprises a polymer chain having the general formula

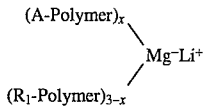

prior to quenching; wherein x is the integer 2 or 3, and A is a functional group derived from an anionic polymerization initiator comprising a lithium amino magnesiate complex having the general formula

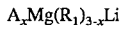

wherein A is selected from the group consisting of cyclic amine substituents having the general formula

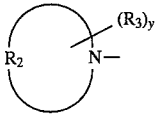

wherein $R_1$, $R_2$, $R_3$, x and y are as described herein above, and the $Mg^-Li^+$ complex is carried at the living ends of up to three polymer chains prior to quenching.

A method according to the invention for preparing a polymer comprises initiating polymerization of at least one monomer selected from diolefin monomers having from about 4 to about 12 carbon atoms, monovinyl aromatic monomers having from about 8 to about 20 carbon atoms, and trienes having from about 10 to about 20 carbons, in the presence of an anionic polymerization initiator comprising a lithium amino magnesiate complex having the general formula

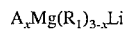

where A, $R_1$ and x are as described herein above.

DETAILED DESCRIPTION OF THE INVENTION

As will become apparent from the description which follows, the present invention provides novel lithium amino magnesiate initiators for anionic polymerization of diene homopolymer and copolymer elastomers. Polymer molecules prepared with these initiators contain a functional group comprising a cyclic amine substituent group derived from the initiator.

It has been unexpectedly discovered herein that vulcanizable elastomeric compounds containing the tertiary amine functionalized polymer molecules of the present invention, and articles made therefrom, exhibit useful properties, particularly reduced hysteresis. When compounded to make products such as tires, power belts and the like, these polymeric products of this invention exhibit increased rebound, decreased rolling resistance and less heat build-up when mechanical stresses are applied.

It has been further unexpectedly found that polymerization employing initiators according to the invention can be conducted at elevated temperatures as high as the peak temperatures resulting from exothermic polymerization reactions, such as from about 49° C. to 149° C. or even higher temperatures. The novel initiators of the present invention provide a magnesium-lithium complex which is carried at the "living" end of the polymer chain, and it is theorized that, because of the intervening magnesium atom, there is a reduced potential for the lithium atom to be involved in metalation reactions or to combine with an alpha-hydrogen atom on the polymer chain and to be eliminated from the living end of the chain as lithium hydride. Hence, the living ends of the polymers are effectively maintained even at high temperatures.

High temperatures of polymerization result in more efficient polymerizations because more monomers can be incorporated into the polymer chain in a given time period than at lower temperatures. In addition, at higher temperatures, termination reactions are improved because of faster reactions at these high temperatures.

The initiators according to the present invention are lithium amino magnesiate complexes having the general formula

where A is selected from the group consisting of cyclic amine substituents having the general formula

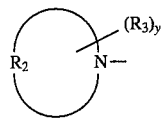

where $R_2$ contains from about 3 to about 20 methylene groups to form a cyclic amine substituent, wherein the nitrogen atoms of at least two of these substituents, which may be the same or different from each other, are covalently bonded to the magnesium atom. The methylene groups in $R_2$ can be substituted with preferably an alkyl $R_3$ group, having from about 1 to about 20 carbons. Either none, a part or all of the methylenes in $R_2$ may be substituted and, therefore, "y" is an integer of from zero to about 10. Where y is greater than zero, the $R_3$ substituents may be the same or mixtures of different substituents. For example, when y is zero, all of the methylenes are —$CH_2$— groups; and when y is 1, one of the methylenes is a —$CHR_3$. Exemplary cyclic amine substituents are hexamethyleneimino, pyrrolidino, piperidino and dodecamethyleneimino. In a typical embodiment, $R_2$ contains about 6 to about 15 methylene groups. In a preferred embodiment of the present invention, y is zero, $R_2$ contains 6 methylene groups and A is hexamethyleneimine (HMI).

The $A_x$ substituents of the initiator complex may be the same or mixtures of different cyclic amine substituents. When x is 2, the initiator complex will be herein referred to as a "type A initiator" and is represented by the formula

$A_2$—$Mg^-$—$(R_1)$—$Li^+$ where $R_1$ can be the same as or different from $R_3$ above, but preferably is an alkyl group, having from about 1 to about 20 carbon atoms. In a preferred embodiment, $A_2$ is $(HMI)_2$ and $R_1$ is an n-butyl group derived from n-butyl lithium. Hence, the preferred type A initiator is $HMI_2Mg^-BuLi^+$, which may be depicted as follows:

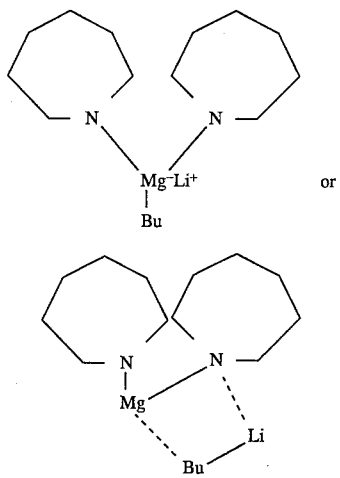

When x is 3, $R_1$ is absent from the initiator complex, and the complex will be herein referred to as a "type B initiator" represented by the general formula

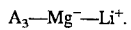

$A_3$—$Mg^-$—$Li^+$.

In a preferred embodiment, $A_3$ is $(HMI)_3$. Hence the preferred type B initiator is $HMI_3Mg^-Li^+$, which may be depicted as follows:

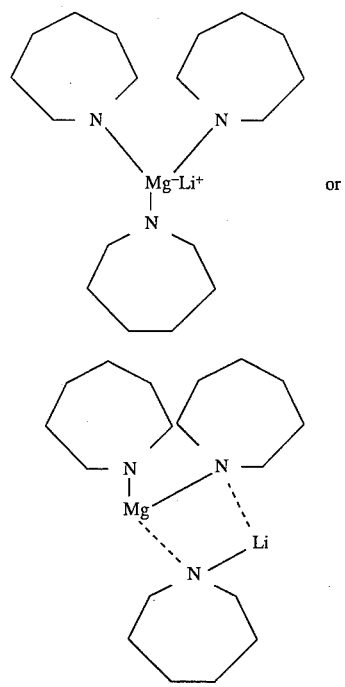

The following examples illustrate methods of preparation of the anionic polymerization initiators of the present invention. However, the examples are not intended to be limiting, as other methods for preparing these initiators may be determined by those skilled in the art. The initiators according to the present invention may be prepared by reacting an organolithium compound having the general formula $R_1Li$, with a magnesium dicyclic amide having the general formula $A_2Mg$, where $R_1Li$ and $A_2Mg$ employ A and $R_1$ as described above. The magnesium dicyclic amide may first be prepared by reacting, for example, a dialkyl magnesium compound with two molecules of the compound AH, and the cyclic amines AH may be the same or different from each other. For example, magnesium dihexamethyleneamide may be prepared by reacting a dibutyl magnesium with two hexamethyleneamine molecules according to the following reaction:

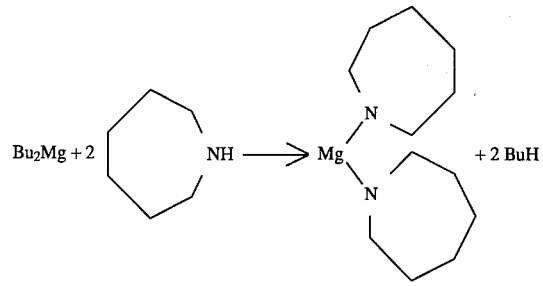

Where $R_1Li$ is, for example, an alkyl lithium, the type A initiator may be prepared by reacting an n-butyl lithium with magnesium dihexamethyleneamide, to form the type A initiator complex, $HMI_2Mg^-BuLi^+$. The reaction forming the preferred type A initiator can, thus, be depicted as follows:

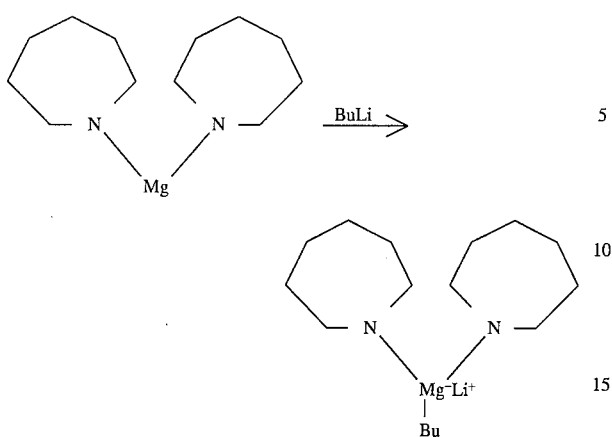

The type B initiator may be derived from the type A initiator by further reacting the type A initiator complex with another AH molecule. For instance, in the preferred embodiment, a further hexamethyleneamine is reacted with $HMI_2Mg^-BuLi^+$ to form the reaction product $HMI_3Mg^-Li^+$. The reaction can be depicted as follows:

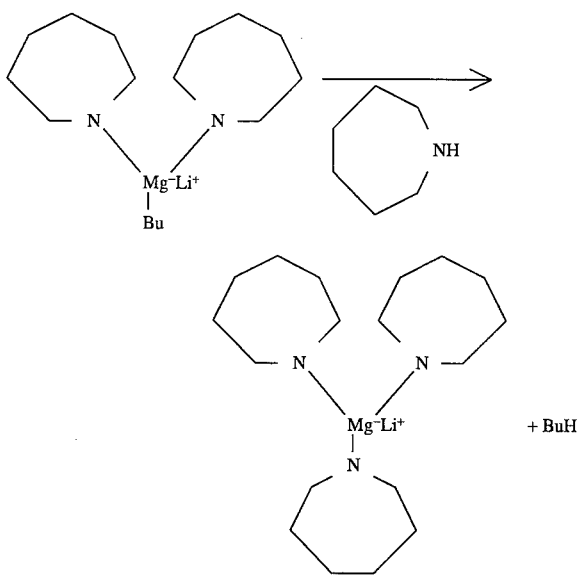

Alternatively, where the organolithium compound is A-lithium, the type B initiator of the preferred embodiment may be prepared by reacting lithium hexamethyleneimide with magnesium dihexamethyleneamide, to form the type B initiator complex, $HMI_3Mg^-Li^+$. The reaction forming the preferred type B initiator can, thus, be depicted as follows:

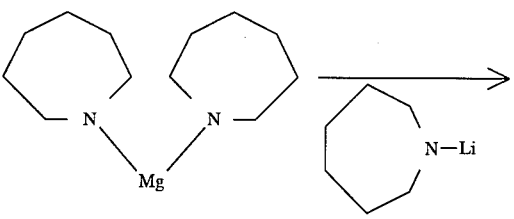

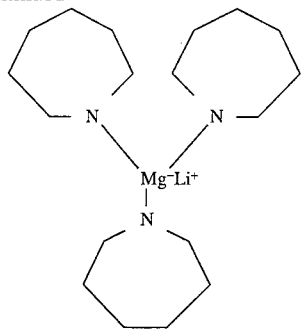

In general, the initiators, according to the present invention, can be prepared, under anhydrous and anaerobic conditions, by forming a solution of the cyclic amine substituent, AH, in an anhydrous, aprotic solvent, such as cyclohexane or hexane in a dry nitrogen atmosphere. To this solution is then added a dialkyl magnesium compound in the same or a similar solvent, followed by the addition of an organolithium compound $R_1Li$ in the same or a similar solvent. If the $R_1Li$ is, for instance, an alkyl lithium, as described herein above, the resulting initiator is a type A initiator. The type B initiator may then be prepared from the type A initiator by adding additional AH, in the same or a similar solvent, to the type A initiator solution. Alternatively, a type B initiator may be prepared by adding an organolithium compound R*Li, where R*Li is A-lithium, to the solution of the $A_2Mg$ compound, as described above.

The amounts of the cyclic amine substituent AH and the magnesium and lithium reactants range from about 2.01 to about 2.10 millimoles (mM) of the amine compound to about 1.0 mM of the magnesium compound and about 1.0 to about 1.1 mM of the lithium compound, with 2.02 mM of the amine compound to 1.0 mM of the magnesium compound to 1.05 mM of the lithium compound preferred. The various reaction temperatures and times which may be employed in the above reactions are known to one skilled in the art. Furthermore, other polar aprotic solvents, such as tertiary amines and various ethers may be added to give a soluble initiator and enhanced reactions.

The initiator, thus prepared, is employed with any anionically-polymerizable monomer to yield polymeric products. Typically, the initiator is used to polymerize unsaturated hydrocarbon monomers such as butadiene, isoprene and the like, and copolymers thereof with monovinyl aromatics such as styrene, alpha methyl styrene and the like, or trienes such as myrcene. Thus, the elastomeric products include diene homopolymers from monomer A and copolymers thereof with monovinyl aromatic monomers B. Exemplary diene homopolymers are those prepared from diolefin monomers having from 4 to about 12 carbon atoms. Exemplary vinyl aromatic copolymers are those prepared from monomers having from 8 to about 20 carbon atoms. Preferred elastomers include diene homopolymers, such as polybutadiene and polyisoprene and copolymers, such as styrene butadiene rubber (SBR). Copolymers can comprise from about 99 to 10 percent by weight of diene units and from about 1 to about 90 percent by weight of monovinyl aromatic or triene units, totalling 100 percent. The polymers and copolymers of the present invention may have 1,2-microstructure contents ranging from about 10 to about 80 percent, with the preferred polymers or copolymers having 1,2-microstructure contents of from about 25 to 65 percent, based upon the diene content.

The elastomeric copolymers are preferably random copolymers which result from simultaneous copolymerization of the monomers A and B with randomizing agents, as is known in the art. Block copolymers, poly (b-B-b-A-b-B), result from the separate polymerization of the monomers forming the A and B polymers as is known in the art. Often, such block copolymers which include poly(b-styrene-b-butadiene-b-styrene) are thermoplastic elastomers, sometimes referred to as S-B-S polymers.

The initiators of the present invention form "living polymers" from the foregoing monomers, the general formula of which is

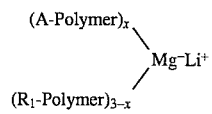

wherein x is the integer 2 or 3, A is a functional group derived from the initiator, the polymer is any of the foregoing diene homopolymers, monovinyl aromatic homopolymers, diene/monovinyl aromatic random copolymers and block copolymers, and the $Mg^-Li^+$ complex is carried at the living ends of up to three polymer chains prior to quenching.

Polymerization is usually conducted in a conventional solvent for anionic polymerizations, such as hexane, cyclohexane, benzene and the like. Various techniques for polymerization, such as semi-batch and continuous polymerization may be employed. In order to promote randomization in copolymerization and to increase vinyl content, a polar coordinator may optionally be added to the polymerization ingredients. Amounts range between about 0.1 to about 90 or more equivalents per equivalent of magnesium and lithium. The amount depends upon the type of polar coordinator that is employed, the amount of vinyl desired, the level of styrene employed and the temperature of the polymerizations, as well as the selected initiator.

Compounds useful as polar coordinators are organic and include tetrahydrofuran, linear and cyclic oligomeric oxolanyl alkanes such as 2-2'-di(tetrahydrofuryl) propane, dipiperidyl ethane, hexamethylphosphoramide, N-N'-dimethylpiperazine, diazabicyclooctane, dimethyl ether, diethyl ether, tributylamine and the like. The linear and cyclic oligomeric oxolanyl alkane polar coordinators are described in U.S. Pat. No. 4,429,091, the subject matter of which regarding polar coordinators is incorporated herein by reference. Other compounds useful as polar coordinators include those having an oxygen or nitrogen hetero-atom and a non-bonded pair of electrons. Examples include dialkyl ethers of mono and oligo alkylene glycols; "crown" ethers; and tertiary amines, such as tetramethylethylene diamine (TMEDA).

Polymerization is begun by charging a blend of the monomer(s) and solvent to a suitable reaction vessel, followed by the addition of the polar coordinator and the initiator previously described. The procedure is carried out under anhydrous, anaerobic conditions. Often, it is conducted under a dry, inert gas atmosphere. The polymerization can be carried out at any convenient temperature, such as about 0° C. to about 149° C. For batch polymerizations, it is preferred to maintain the peak temperature at from about 49° C. to about 149° C., and more preferably from about 80° C. to about 120° C. Polymerization is allowed to continue under agitation for about 0.15 to 24 hours. After polymerization is complete, the product is terminated by a quenching agent, an endcapping agent and/or a coupling agent, as described herein below. The terminating agent is added to the reaction vessel, and the vessel is agitated for about 0.5 to about 4.0 hours. Quenching is usually conducted by stirring the polymer and quenching agent for about 0.25 hours to about 1.0 hour at temperatures of from about 30° C. to about 120° C. to ensure a complete reaction. Polymers terminated with a functional group, as discussed herein below, are subsequently quenched with alcohol or other quenching agent as also described herein below.

Lastly, the solvent is removed from the polymer by conventional techniques such as drum drying, extruder drying, vacuum drying or the like, which may be combined with coagulation with water, alcohol or steam. If coagulation with water or steam is used, oven drying may be desirable.

One way to terminate the polymerization reaction is to employ a protic quenching agent to give a monofunctional polymer chain. Quenching may be conducted in water, steam or an alcohol such as isopropanol, or any other suitable method.

Quenching may also be conducted with a functional terminating agent, resulting in a difunctional polymer. Any compounds providing terminal functionality (e.g., "endcapping") that are reactive with the polymer bound carbon-magnesium-lithium moiety can be selected to provide a desired functional group. Examples of such compounds are alcohols, substituted aldimines, substituted ketimines, Michler's ketone, 1,3-dimethyl-2-imidazolidinone, 1-alkyl substituted pyrrolidinones, 1-aryl substituted pyrrolidinones, tin tetrachloride, tributyl tin chloride, carbon dioxide, and mixtures of these. Further examples of reactive compounds include the terminators described in U.S. Pat. No. 5,066,729 and in U.S. Pat. No. 5,521,309, the subject matter of which, pertaining to terminating agents and terminating reactions, is hereby incorporated by reference. The practice of the present invention is not limited solely to these terminators, since other compounds that are reactive with the polymer bound carbon-magnesium-lithium moiety can be selected to provide a desired functional group. Preferred endcapping agents are tin tetrachloride and dibutyl tin dichloride.

While terminating to provide a functional group on the terminal end of the polymer is preferred, it is further preferred to terminate by a coupling reaction with, for example, tin tetrachloride or other coupling agent such as silicon tetrachloride or esters. High levels of tin coupling are desirable in order to maintain good processability in the subsequent manufacturing of rubber products. Further, it is known that when polymers are compounded as, for example, in the formulation shown in TABLE VII, compound viscosities are increased significantly. To attain manageable compound viscosities, lower molecular weight polymers must be used. However, these lower molecular weights result in both cold and hot flow problems during manufacturing processes and polymer storage. A known remedy for these problems is to tin couple the living anionic polymers using, for example, tin tetrachloride.

As stated above, it has been found that the invention initiators provide for polymers having living ends maintained thereon, even at high polymerization temperatures. This allows effective and efficient tin coupling using tin tetrachloride, which results in a functionalized polymer having improved processability and resistance to hot and cold flow. It is preferred that the polymers according to the present invention have at least about 40 percent tin coupling. That is, about 40 percent of the polymer mass after coupling is of higher molecular weight than the polymer before coupling as measured, for example, by gel permeation chromatography.

As noted above, various techniques known in the art for carrying out polymerizations may be used with these initiators without departing from the scope of the present invention.

The polymers of the present invention contain a functional group derived from the initiator at the head (initiator) end of the polymer chain, in addition to an optional functionality (derived from the terminating agent or coupling agent) at the terminal end of the chain. These functional groups have an affinity for compounding filler materials such as silica or carbon black. Such compounding results in products exhibiting reduced hysteresis, which means a product having increased rebound, decreased rolling resistance and lessened heat build-up when subjected to mechanical stress. Products including tires, power belts and the like are envisioned. Decreased rolling resistance is, of course, a useful property for pneumatic tires, both radial as well as bias ply types and thus, the vulcanizable elastomeric compositions of the present invention can be utilized to form treadstocks for such tires. The composition can also be used to form other elastomeric tire components such as subtreads, black sidewalls, body ply skims, bead fillers and the like.

The polymers of the present invention can be utilized as 100 parts of the rubber in the treadstock compound, or they can be blended with any conventionally employed treadstock rubber which includes natural rubber, synthetic rubber and blends thereof. When the polymers of the present invention are blended with conventional rubbers, the amounts can vary widely with a lower limit comprising about 10 to 20 percent by weight of the total rubber. The minimum amount will depend primarily upon the degree of hysteresis reduction desired. Thus, the compounds can contain 10–100% by weight of the inventive polymer, with the balance, if any, being a conventional rubber.

The polymers can be compounded with all forms of carbon black in amounts ranging from about 5 to 80 parts by weight, per 100 parts of rubber (phr), with about 35 to 60 phr being preferred. The carbon blacks may include any of the commonly available, commercially-produced carbon blacks. Examples of preferred carbon black compounds are described in U.S. Pat. No. 5,521,309, the subject matter of which, relating to carbon black compounds, is incorporated by reference herein. Silica can be used in place of all or part of the carbon black.

The reinforced rubber compounds can be cured in a conventional manner with known vulcanizing agents at about 0.1 to 10 phr. For a general disclosure of suitable vulcanizing agents, one can refer to Kirk-Othmer, *Encyclopedia of Chemical Technology*, 3rd ed., Wiley Interscience, N.Y. 1982, Vol. 20, pp. 365–468, particularly "Vulcanization Agents and Auxiliary Materials", pp. 390–402. Vulcanizing agents can be used alone or in combination.

Vulcanizable elastomeric compositions of the invention can be prepared by compounding or mixing the functionalized polymers herein with carbon black and other conventional rubber additives including, for example, fillers, such as silica, plasticizers, antioxidants, curing agents and the like, using standard rubber mixing equipment and procedures. Such elastomeric compositions, when vulcanized using conventional rubber vulcanization conditions, have reduced hysteresis properties and are particularly adapted for use as tread rubbers for tires having reduced rolling resistance.

EXAMPLES AND GENERAL EXPERIMENTAL PROCEDURE

In order to demonstrate the preparation and properties of elastomers prepared according to the present invention, a number of initiators were prepared. The initiators were then used to polymerize a solution of styrene and butadiene monomers. For comparison, polymerizations employing butyllithium, lithium hexamethyleneimide, dibutyllithium magnesium hexamethyleneimide initiators were also carried out.

A listing of abbreviations, compound names and structures as used in the following examples and tables is provided in TABLE I.

TABLE I

| | Abbreviations/Compounds/Structures | |
|---|---|---|
| Abbreviation | Compound | Structure |
| BuLi | n-butyllithium | $CH_3CH_2CH_2CH_2Li$ |
| HMI-Li | lithium hexamethyleneimide | (ring)N—Li |
| HMI-Mg$^-$Bu$_2$-Li$^+$ | lithium dibutyl hexamethyleneimino magnesiate | (ring)N—Mg$^-$Li$^+$ with two Bu groups on Mg |

TABLE I-continued

Abbreviations/Compounds/Structures

| Abbreviation | Compound | Structure |
|---|---|---|
| HMI$_2$Mg$^-$BuLi$^+$ | lithium butyl dihexamethyleneimino magnesiate | (structure shown) |
| HMI$_3$Mg$^-$Li$^+$ | lithium trihexamethyleneimino magnesiate | (structure shown) |

Initiator Preparation

1. Type A Initiator (HMI$_2$Mg$^-$BuLi$^+$)

In order to prepare the HMI$_2$Mg$^-$BuLi$^+$, 10 ml of a 1.0 molar (M) solution of dibutyl magnesium in heptane was added (via syringe) to 2.0 grams (20.16 millimoles (mM)) of distilled hexamethyleneamine (HMI) in 43 ml. of dry cyclohexane in a 7 ounce, nitrogen-filled beverage bottle capped with a rubber liner and a crown two-hole cap. The mixture was then placed on a shaker for about 5 minutes. To the shaken mixture was then added, via syringe, 6.42 ml. of a 1.636M hexane solution of butyllithium (10.5 mM) and the mixture was again briefly shaken to allow the solids to go into solution.

2. Type B Initiator (HMI$_3$Mg$^-$Li$^+$)

The HMI$_3$Mg$^-$Li$^+$ initiator was prepared by the same procedure as that for the type A initiator except that, following the addition of the butyllithium and the brief shaking of the mixture, a further 10.08 mM of hexamethyleneamine (HMI) were added.

After preparation, the preformed initiators type A and type B were found to be stable at room temperature for at least seven weeks.

3. Type C Initiator (HMI-Mg$^-$Bu$_2$Li$^+$)

This initiator was prepared for purposes of comparison only. It is not an initiator of the invention. The initiator was prepared in a similar manner to the type A initiator described herein above, except that, in this case, one mole of dibutyl magnesium was reacted with one mole of lithium hexamethyleneimide.

Polymer Preparations

In each of the following examples, the polymer was prepared in a 28 ounce beverage bottle. The bottles were baked for at least 24 hours at 115° C. and then capped with crown, two-hole caps and rubber liners. The bottles were cooled while purging with nitrogen.

Polymer 1

To the bottle described herein above, was charged 266.1 grams of a blend of 19.4 weight percent 1,3-butadiene/styrene (74/26 by weight) in hexane. To this blend was added 0.57 ml. of a 0.5M solution of 2,2'-di(tetrahydrofuryl) propane in hexane, followed by 2.20 ml. of type A (HMI$_2$Mg$^-$BuLi$^+$) initiator solution. This reaction mixture was placed in an 80° C. constant temperature water bath, equipped with an agitator, and agitated for 20 minutes.

To the resultant viscous polymer solution was added 0.41 ml. of a 0.25M solution of tin tetrachloride in hexane. The mixture was then placed in a 50° C. constant temperature water bath and agitated for 1.33 hours. To the mixture was then added 1 ml. of isopropanol and 4 ml. of a di-t-butyl-p-cresol (DBPC) solution (80 grams of DBPC in 700 ml. hexane). The DBPC solution served as an antioxidant to prevent degradation of the polymer. The polymer was isolated by coagulation in 1100 ml. of isopropanol and then dried in a vacuum oven at 55° C.

Polymer 2

To a bottle, as described herein above, was charged 254.6 grams of a blend of 19.4 weight percent 1,3-butadiene/styrene (74/26 by weight) in hexane. To this blend was added 0.59 ml. of a 0.5M solution of 2,2'-di(tetrahydrofuryl) propane in hexane, 0.395 ml. of a 1.0M solution of hexamethyleneamine in hexane and 0.30 ml. of a 1.636M solution of n-butyllithium in hexane. This reaction mixture was agitated for 20 minutes in an 80° C. constant temperature water bath.

To the resultant viscous polymer solution was added 0.395 ml. of a 0.25M solution of tin tetrachloride in hexane. The mixture was then placed in a 50° C. constant temperature bath and agitated for 1.33 hours. Following the addition of 1 ml. isopropanol and 4 ml. of DBPC solution (80 grams of DBPC in 700 ml. of hexane), the polymer was isolated by coagulation in 1100 ml. of isopropanol and then dried in a vacuum oven at 55° C.

Polymers 3–6

The procedure for preparation of polymers 3 and 5, and polymers 4 and 6 was the same as that used for polymers 1 and 2, respectively, except for variations in the 80° C. polymerization times (as shown in TABLE II).

Polymer 7

To the bottle described herein above, was charged 263.9 grams of a blend of 19.4 weight percent 1,3-butadiene/styrene (74/26 by weight) in hexane. To this blend was added 0.56 ml. of a 0.5M solution of 2,2'-di(tetrahydrofuryl) propane in hexane, followed by 2.18 ml. of type A ($HMI_2Mg^-BuLi^+$) initiator solution. This reaction mixture was agitated in an 80° C. constant temperature water bath for 40 minutes.

To the resultant viscous polymer solution was added 0.41 ml. of a 0.25M solution of tin tetrachloride in hexane. The mixture was then placed in a 50° C. constant temperature water bath and agitated for 1 hour and 25 minutes.

Following the addition of 1 ml. of isopropanol and 4 ml. of DBPC solution (80 grams of DBPC in 700 ml. of hexane), the polymer was isolated by coagulation in 1100 ml. of isopropanol and then dried in a vacuum oven at 55° C.

Polymer 8

To the bottle described herein above, was charged 257.1 grams of a blend of 19.4 weight percent 1,3-butadiene/styrene (74/26 by weight) in hexane. To this blend was added 0.50 ml. of a 0.5M solution of 2,2'-di(tetrahydrofuryl) propane in hexane, followed by 2.16 ml. of type B ($HMI_3Mg^-Li^+$) initiator solution. This reaction mixture was agitated in an 80° C. constant temperature water bath for 40 minutes.

To the resultant viscous polymer solution was added 0.40 ml. of a 0.25M solution of tin tetrachloride in hexane. The mixture was then placed in a 50° C. constant temperature water bath and agitated for 1 hour and 25 minutes.

Following the addition of 1 ml. of isopropanol and 4 ml. of a DBPC solution (80 grams of DBPC in 700 ml. of hexane), the polymer was isolated by coagulation in 1100 ml. of isopropanol and then dried in a vacuum oven at 55° C.

Polymers 9 and 10

The procedure for the preparation of polymers 9 and 10 was essentially the same as that used for polymers 7 and 8, respectively, except that both the type A and the type B initiators were aged at room temperature for seven weeks before being used in the polymerization reaction.

Polymers 11 and 12

Polymers 11–12 were prepared by essentially the same procedure as that used to prepare polymer 7, except that polymer 11 was prepared with the type C initiator ($HMI-Mg^-Bu_2Li^+$) and polymer 12 was prepared with the type A initiator ($HMI_2Mg^-BuLi+$).

Polymers 13 through 16

Polymers 13–16 were prepared by essentially the same general procedures as those described herein above. The initiators used and the time and temperature of the polymerization reaction were varied, as presented in TABLE V. Polymers 14 and 15 were terminated with the coupling agent, tin tetrachloride. Polymers 13 and 16 were terminated only with alcohol.

Polymers 17 and 18

These polymers were prepared by essentially the same general procedures as those described herein above, except that the polymerization reaction was carried out at 66° C. for 3 hours. Polymer 17 was then chain-end functionalized with tin tetrachloride as described above. In contrast, polymer 18 was chain-end functionalized with a combination of tributyl tin chloride and carbon dioxide. Tributyl tin chloride was added first to the polymer solution, in an amount sufficient to terminate 30 percent of the active initiator. After briefly shaking the bottle (about 1 minute), carbon dioxide was pressured into the bottle to a pressure of 62 psi. After a further brief shaking of the bottle (about 20 seconds), the carbon dioxide addition was repeated twice more. The polymer, after treatment with DBPC, was isolated by coagulation in isopropanol and thereafter was vacuum oven-dried at 55° C.

Polymer Evaluations

A comparison of the properties of SBR polymers made with the type A initiator and terminated with tin tetrachloride, and those of polymers made with a comparative, non-invention lithium HMI initiator are shown in TABLE II. As shown in the table, the percent yield (the ratio of the monomers polymerized to the monomers charged) is almost 100 percent in just a 40 minute polymerization time at 80° C. In addition, the invention polymers show a high level of tin coupling (greater than the preferred 40% coupling). This is also shown by the higher average molecular weights (Mn coupled) of the tin-coupled polymer, compared to the polymer terminated with alcohol alone (Mn base). The invention polymers and the non-invention polymers show comparable levels of HMI content.

To determine if the target property of reduced hysteresis was met by the invention polymers, a value of tan delta at 50° C. was determined. Tan delta is a measure of the ratio of the loss modulus of the compound to the storage modulus and it has been found that the lower the magnitude of tan delta, the lower is the hysteresis of the compound. As shown in TABLE II, the polymers prepared with the type A initiator of the invention showed an improvement, i.e. a reduction in the tan delta values, over the control lithium HMI initiated polymers, while still maintaining high levels of tin coupling (greater than 40%).

A comparison of the properties of SBR polymers made with type A and type B initiators is shown in TABLE III. Polymer 8, made with the type B initiator, shows a further reduction in tan delta and, therefore, a further reduction in hysteresis in comparison with polymer 7, made with the type A initiator. In addition, the ratio of the weight average molecular weight to the number average molecular weight (Mw/Mn) shows that both polymers have a desirable narrow range of molecular weight distribution. Polymer 8 shows a higher percentage of HMI incorporation than polymer 7, thus showing that the extra HMI group provided by the type B initiator is incorporated into the polymer. Both polymers show comparable high tin coupling. Polymers 9 and 10 were made with initiators that had been aged at room temperature for 7 weeks. The results, which are comparable with those of polymers 7 and 8, illustrate the stability of the initiators. The Mn and Mw/Mn values for polymers 9 and 10 were obtained on samples taken just prior to the tin tetrachloride coupling reaction and they were terminated with isopropanol.

In TABLE IV, a comparison is made of properties of polymers made with type A initiators and type C initiators. The results show that the type C initiators are not very effective for hysteresis reduction, probably because of very low incorporation of HMI in the polymer chain.

The polymers illustrated in TABLE V are monofunctionalized polymers (polymers 13–15) and a nonfunctionalized polymer (polymer 16). In the table, zero percent coupling indicates a polymer which was not reacted with tin tetrachloride, but rather was terminated with isopropanol. Polymer 13, initiated with a type-B initiator, derives its functional end group (HMI) from the initiator. This polymer also exhibits a high glass transition temperature, indicating that this sample had a higher 1,2-butadiene structural content than the other examples. Higher 1,2-butadiene content and higher glass transition temperatures generally result in higher tan delta values. The results illustrated in TABLE V show the effectiveness of the HMI functional group (derived from the invention initiators) at the head end of the polymer chain. The tan delta (50° C.) value for polymer 13 is much better in comparison with the tan delta for the polymer containing no functional groups (polymer 16) and very comparable with the tan delta values for polymers containing tin functionality at the terminal end of the polymer (polymers 14 and 15).

As shown in TABLE VI, polymers produced using the invention initiators can be terminated with a different functionalizing agent (tributyl tin chloride and carbon dioxide). Polymer 18, terminated with this agent, shows a further reduction in tan delta, and thus hysteresis, in comparison with polymer 17, which was terminated with tin tetrachloride.

Vulcanization of Elastomers

All of the elastomers of this invention were compounded in a standard test formulation shown in TABLE VII. This formulation yields low tan deltas and, therefore, is especially valuable for comparing hysteresis of different polymers. All of the compound mixes were prepared in a small Brabender mixer. Besides the critical tan delta property, stress-strain properties of the vulcanized elastomers were also obtained in order to ascertain good cures. TABLE VIII shows stress/strain data for vulcanizates made from the test formulation of TABLE VII. Samples were cured for 20 minutes at 165° C. All of the SBR polymers were random copolymers, i.e., styrene distribution was random or non-block, with 20–25 percent by weight of styrene.

In conclusion, it is clear from the foregoing examples and specification disclosure that the initiators of the present invention are useful for the anionic polymerization of diene monomers at elevated temperatures, and for the incorporation of up to 100 percent of the initially charged monomers into the polymer. The resulting elastomeric polymers contain functional cyclic amine groups, derived from the initiator, at the site of initiation and a magnesium-lithium complex at the terminal, "living" end. After quenching, the polymers still retain the functional group at the site of initiation. The functional group promotes uniform and homogeneous mixing with carbon black. As a result, vulcanizable elastomeric compounds containing these polymers exhibit improved hysteresis, which provides lower rolling resistance in tires and improved fuel economy. Additionally, the magnesium-lithium terminated polymers can be quenched with compounds to provide terminal functional groups and hence, multifunctional polymer chains. The polymers also exhibit improved tin tetrachloride coupling after high temperature polymerizations.

The invention is not limited to the specific reactants, initiators, and organomagnesium and organolithium compounds disclosed, nor to any particular modifier or solvent. Similarly, the examples have been provided merely to demonstrate the practice of the subject invention and do not constitute limitations of the invention. Those skilled in the art may readily select other monomers and process conditions, according to the disclosure made herein above. Thus, it is believed that any of the variables disclosed herein can readily be determined and controlled without departing from the scope of the invention herein disclosed and described. Moreover, the scope of the invention shall include all modifications and variations that fall within the scope of the attached claims.

TABLE II

Properties of SBR Polymers Made At 80° C. With Type A Initiators/SnCl$_4$ Couping

| Polymer | Initiator | Min. @ 80° C. | Tg, °C. | % Yield | % Coupling | Mn × 10$^{-3}$ Base | Mn × 10$^{-3}$ Cpled | % HMI | 50° C. Tan δ |
|---|---|---|---|---|---|---|---|---|---|
| 1 | HMI$_2$Mg$^-$BuLi$^+$ | 20 | −34 | 78.7 | 47.3 | 117 | 365 | 67 | N.D.$^{(a)}$ |
| 2 | LHMI$^{(b)}$ | 20 | −44 | 99.2 | 33.2 | 139 | 404 | 58 | 0.105 |
| 3 | HMI$_2$Mg$^-$BuLi$^+$ | 40 | −33 | 96.4 | 43.6 | 140 | 395 | 50 | 0.094 |
| 4 | LHMI$^{(b)}$ | 40 | −45 | 99.0 | 26.5 | 124 | 323 | 47 | 0.108 |
| 5 | HMI$_2$Mg$^-$BuLi$^+$ | 60 | −35 | 100.0 | 42.4 | 146 | 428 | 49 | 0.096 |
| 6 | LHMI$^{(b)}$ | 60 | −44 | 99.0 | 25.8 | 130 | 342 | 49 | 0.113 |

$^{(a)}$Tan δ not determined due to low percent yield.
$^{(b)}$Comparative, i.e., non-invention examples.

TABLE III

Comparison of Properties of SBR Polymers Made at 80° C.
With Type A and Type B Initiators/SnCl$_4$ Coupling[a]

| Polymer | Initiator | Tg, °C. | Mn (total) | Mn (base) | Mw/Mn | % Coupling | % HMI | 50° C. Tan δ |
|---|---|---|---|---|---|---|---|---|
| 7 | HMI$_2$Mg$^-$BuLi$^+$ | −34.5 | 191,372 | | 1.48 | 49.7 | 34 | 0.104 |
| 8 | HMI$_3$Mg$^-$Li$^+$ | −35.0 | 190,875 | | 1.53 | 48.6 | 60 | 0.089 |
| 9 | HMI$_2$Mg$^-$BuLi$^{+[b]}$ | −36.9 | | 106,311 | 1.32 | 45 | 45 | 0.109 |
| 10 | HMI$_3$Mg$^-$Li$^{+[b]}$ | −40.9 | | 113,580 | 1.26 | 64 | 64 | 0.092 |

[a]40 minute polymerization time.
[b]These initiators were aged for 7 weeks before use.

TABLE IV

Comparison of Properties of SBR Polymers Made at 80° C.
With Type A and Type C Initiators/SnCl$_4$ Coupling[a]

| Polymer | Initiator | Tg, °C. | Mn | Mw/Mn | % Coupling | % HMI | 50° C. Tan δ |
|---|---|---|---|---|---|---|---|
| 11 | HMIMg$^-$Bu$_2$Li$^{+[b]}$ | −34.5 | 151,742 | 1.54 | 65 | 18 | 0.134 |
| 12 | HMI$_2$Mg$^-$BuLi$^+$ | −32.0 | 139,620 | 1.72 | 42 | 75 | 0.107 |

[a]40 minute polymerization time.
[b]Comparative, i.e., non-invention example.

TABLE V

Properties of SBR Polymers Containing Only One or No Functional End Group

| Polymer | Initiator | Polymerization Temperature/Time | Tg, °C. | M$_n$ | % Tin Coupling | 50° C. Tan δ |
|---|---|---|---|---|---|---|
| 13 | HMI$_3$Mg$^-$Li$^+$ | 50° C./12 hours | −20 | 139,752 | 0 | 0.107 |
| 14 | BuLi[a] | 80° C./40 minutes | −35 | 211,230 | 64 | 0.116 |
| 15 | BuLi[a] | 80° C./60 minutes | −36 | 190,796 | 56 | 0.124 |
| 16 | BuLi[b] | 80° C./60 minutes | −35 | 111,620 | 0 | 0.183 |

[a]Comparative, i.e., non-invention example of a mono-functionalized (tin-functionalized) polymer.
[b]Comparative, i.e., non-invention example of a non-functionalized polymer.

TABLE VI

Comparison of Properties of SBR Polymers Functionalized With A Different Terminating Agent

| Polymer | Initiator | Terminator | Tg, °C. | 50° C. Tan δ |
|---|---|---|---|---|
| 17 | HMI$_2$Mg$^-$Li$^+$ | SnCl$_4$ | −30 | 0.106 |
| 18 | HMI$_2$Mg$^-$Li$^+$ | Bu$_3$SnCl/CO$_2$ | −29 | 0.098 |

TABLE VII

Compounding Test Formulation

| COMPONENT | PARTS BY WEIGHT |
|---|---|
| Polymer | 100 |
| Carbon (N-351) | 55 |
| Naphthenic Oil | 10 |
| Zinc Oxide | 3 |
| Antioxidant | 1 |
| Wax | 2 |
| Stearic Acid | 2 |
| Sulfur | 1.5 |
| Accelerator | 1 |

TABLE VIII

Stress/Strain Data For SBR Made at 80° C.
With various Initiators/SnCl$_4$-Coupling

| initiator | Polymer | 300% M, psi | Tensile Strength, psi | Elongation at Break |
|---|---|---|---|---|
| LHMI[a] | 2 | 2286 | 3101 | 378% |
| HMI$_2$Mg$^-$BuLi$^+$ | 3 | 2322 | 3095 | 372% |
| LHMI[a] | 4 | 2235 | 3179 | 394% |
| HMI$_2$Mg$^-$BuLi$^+$ | 5 | 2296 | 2855 | 353% |
| LHMI[a] | 6 | 2268 | 3104 | 383% |
| HMI$_2$Mg$^-$BuLi$^+$ | 7 | 2454 | 3178 | 363% |
| HMI$_3$Mg$^-$Li$^+$ | 8 | 2735 | 3760 | 382% |

TABLE VIII-continued

Stress/Strain Data For SBR Made at 80° C.
With various Initiators/SnCl$_4$-Coupling

| initiator | Polymer | 300% M, psi | Tensile Strength, psi | Elongation at Break |
|---|---|---|---|---|
| HMI$_2$Mg$^-$BuLi$^+$ | 9 | 1932 | 2752 | 391% |
| HMI$_3$Mg$^-$Li$^+$ | 10 | 2039 | 2868 | 385% |

(a)Comparative, i.e., non-invention examples.

We claim:

1. An anionic polymerization initiator comprising a lithium amino magnesiate complex having the formula

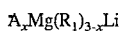

where A is selected from the group consisting of cyclic amine substituents having the formula

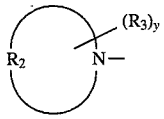

where x is the integer 2 or 3; the A substituents are the same or mixtures of different substituents; R$_2$ is from about 3 to about 20 methylene groups; R$_1$ and R$_3$, which can be the same or different from one another, are selected from the group consisting of alkyls, cycloalkyls, alkenyls, alkynyls, aryls and aralkyls, having from 1 to about 20 carbon atoms; y is an integer of from zero to about 10; and where y is greater than zero, the R$_3$ substituents are the same or mixtures of different substituents.

2. An anionic polymerization initiator, as set forth in claim 1, wherein A$_x$ is (hexamethyleneimine)$_x$, x is 2 or 3, and y is zero.

3. An anionic polymerization initiator, as set forth in claim 1, wherein (R$_1$)$_{3-x}$Li is n-butyl lithium and x is 2.

4. A method of preparing an anionic polymerization initiator, comprising the steps of:

reacting an organolithium compound having the formula R$_1$Li or A-lithium, with a magnesium dicyclic amide having the formula A$_2$Mg, to form a reaction product having the formula

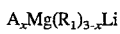

where A is selected from the group consisting of cyclic amine substituents having the formula

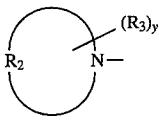

where x is the integer 2 or 3; and wherein when x is 2, the organolithium compound is R$_1$Li and R$_1$ is selected from the group consisting of alkyls, cycloalkyls, alkenyls, alkynyls, aryls and aralkyls having from 1 to about 20 carbon atoms; and when x is 3, the organolithium compound is A-lithium; the A substituents are the same or mixtures of different substituents; R$_2$ is from about 3 to about 20 methylene groups, R$_3$ is selected from the group consisting of alkyls, cycloalkyls, alkenyls, alkynyls, aryls and aralkyls having from 1 to about 20 carbon atoms; y is an integer of from zero to about 10; and where y is greater than zero, the R$_3$ substituents are the same or mixtures of different substituents.

5. The method as set forth in claim 4, wherein when x is 2, the method further comprises the step of reacting said reaction product with compound AH, wherein AH is the cyclic amine form of A.

6. The method as set forth in claim 4, wherein A$_2$Mg is magnesium dihexamethyleneamide.

7. The method as set forth in claim 4, wherein A$_x$ is (hexamethyleneimine)$_x$, x is 2 or 3, and y is zero.

8. The method as set forth in claim 4, wherein R$_1$Li is selected from the group consisting of n-butyl lithium and lithium hexamethyleneimide.

9. A polymer comprising:

a polymer chain having the formula

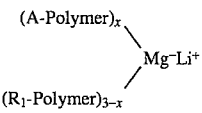

prior to quenching; wherein x in the integer 2 or 3, and A is a functional group derived from an anionic polymerization initiator comprising a lithium amino magnesiate complex having the formula

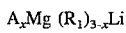

where A is selected from the group consisting of cyclic amine substituents having the formula

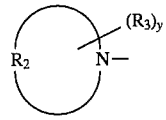

where R$_2$ is from about 3 to about 20 methylene groups; R$_1$ and R$_3$, which can be the same or different from one another, are selected from the group consisting of alkyls, cycloalkyls, alkenyls, alkynyls, aryls and aralkyls having from 1 to about 20 carbon atoms; the A substituents are the same or mixtures of different substituents; x is the integer 2 or 3; y is an integer of from zero to about 10; and where y is greater than zero, the R$_3$ substituents are the same or mixtures of different substituents.

10. A polymer, as set forth in claim 9, wherein A$_x$ is (hexamethyleneimine)$_x$, x is 2 or 3, and y is zero.

11. A polymer, as set forth in claim 9, wherein the polymer component of said polymer chain is selected from diolefin and triene monomers having from about 4 to about 12 carbon atoms, and copolymers of said diolefin and triene monomers together with monovinyl aromatic monomers having from about 8 to about 20 carbon atoms.

12. A vulcanizable elastomer composition formed from the polymer of claim 9 and from about 5 to about 80 parts by weight of carbon black, per 100 parts by weight of the polymer.

13. A tire having at least one component formed from the vulcanizable elastomer composition of claim 12.

14. A method of preparing a polymer comprising the steps of:

polymerizing at least one monomer selected from the group consisting of diolefin monomers having from about 4 to about 12 carbon atoms, monovinyl aromatic monomers having from about 8 to about 20 carbon atoms, and trienes, in the presence of an anionic polymerization initiator comprising a lithium amino magnesiate complex having the formula

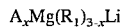

where A is selected from the group consisting of cyclic amine substituents having the formula

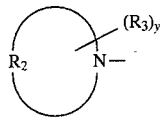

where $R_2$ is from about 3 to about 20 methylene groups; $R_1$ and $R_3$, which can be the same or different from one another, are selected from the group consisting of alkyls, cycloalkyls, alkenyls, alkynyls, aryls and aralkyls having from 1 to about 20 carbon atoms, and mixtures thereof; the A substituents are the same or mixtures of different substituents; x is the integer 2 or 3; y is an integer of from zero to about 10; and where y is greater than zero, the $R_3$ substituents are the same or mixtures of different substituents.

15. A method of preparing a polymer, as set forth in claim 14, wherein said monomer and said initiator are dissolved in an anhydrous aprotic solvent selected from the group consisting of amino and ether solvents.

16. A method of preparing a polymer, as set forth in claim 14, wherein the polymerizing step includes polymerizing at a temperature of from about 49° C. to about 149° C.

17. A method of preparing a polymer, as set forth in claim 14, wherein $A_x$ is (hexamethyleneimine)$_x$, x is 2 or 3, and y is zero.

18. A method, as set forth in claim 14, comprising the further step of terminating said polymerization with a terminating or coupling agent.

19. A method, as set forth in claim 18, wherein said polymerization is terminated with a terminating agent selected from the group consisting of alcohols, substituted aldimines, substituted ketimines, Michler's ketone, 1,3-dimethyl-2-imidazolidinone, 1-alkyl substituted pyrrolidinones, 1-aryl substituted pyrrolidinones, tin tetrachloride, tributyl tin chloride, carbon dioxide, and mixtures thereof.

20. A polymer prepared according to the method of claim 14.

21. A vulcanizable elastomer composition comprising the polymer of claim 20 and from about 5 to 80 parts by weight of carbon black, per 100 parts of the polymer.

22. A tire having at least one component formed from the vulcanizable elastomer composition of claim 21.

23. A functionalized polymer having improved hysteresis properties and coupling ability, said polymer formed by the polymerization of at least one anionically polymerizable monomer, the improvement comprising:

initiating polymerization of at least one monomer selected from diolefin monomers having from about 4 to about 12 carbon atoms, monovinyl aromatic monomers having from about 8 to about 20 carbon atoms, and trienes, at a temperature of from about 49° C. to about 149° C., in the presence of an anionic polymerization initiator comprising a lithium amino magnesiate complex having the formula

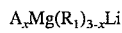

where A is selected from the group consisting of cyclic amine substituents having the formula

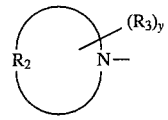

where $R_2$ is from about 3 to about 20 methylene groups; $R_1$ and $R_3$, which can be the same or different from one another, are selected from the group consisting of alkyls, cycloalkyls, alkenyls, alkynyls, aryls and aralkyls having from 1 to about 20 carbon atoms, and mixtures thereof; the A substituents are the same or mixtures of different substituents; x is the integer 2 or 3; y is an integer of from zero to about 10; and where y is greater than zero, the $R_3$ substituents are the same or mixtures of different substituents.

* * * * *